United States Patent [19]

Beriger

[11] 4,078,075
[45] Mar. 7, 1978

[54] INSECTICIDALLY ACTIVE 3-N-(4-TRIFLUOROMETHYLPHENYL)-CARBAMOYL-4-HYDROXY-COUMARIN

[75] Inventor: Ernst Beriger, Allschwil, Switzerland

[73] Assignee: Ciba-Geigy Corporation, Ardsley, N.Y.

[21] Appl. No.: 780,896

[22] Filed: Mar. 24, 1977

Related U.S. Application Data

[63] Continuation-in-part of Ser. No. 724,829, Sep. 20, 1976, abandoned.

[51] Int. Cl.² .......................................... C07D 311/22
[52] U.S. Cl. ............................ 424/281; 260/343.45
[58] Field of Search .................... 260/343.45; 424/281

[56] References Cited

U.S. PATENT DOCUMENTS

| B 587,786 | 2/1976 | Pankavich | 424/281 |
| 2,127,879 | 8/1938 | Martin | 260/343.2 R |
| 3,122,557 | 2/1964 | Molho | 260/295 |

*Primary Examiner*—Norma S. Milestone
*Attorney, Agent, or Firm*—Harry Falber

[57] ABSTRACT

The compound of the formula I

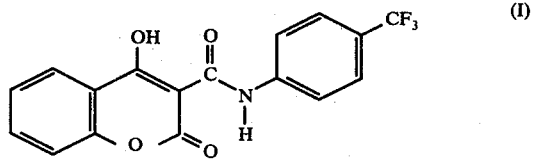

exhibits valuable insecticidal properties and is in particular useful for combating pests of the species *Heliothis virescens* in cotton cultures.

8 Claims, No Drawings

INSECTICIDALLY ACTIVE 3-N-(4-TRIFLUOROMETHYLPHENYL)-CARBAMOYL-4-HYDROXY-COUMARIN

CROSS REFERENCE

This application is a continuation in part of our application Ser. No. 724,829 filed 09/20/76, now abandoned.

DETAILED DISCLOSURE

The present invention relates to the compound 3-N-(4-trifluoromethylphenyl)-carbamoyl-4-hydroxy-coumarin of the formula I

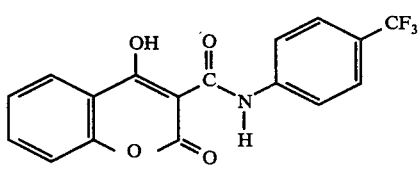

insecticidal compositions containing this compound and its use in combating insect pests particularly of the species Heliothis virescens, a prevelant and persistant species of major concern and causing wide-spread and extensive damage to cotton crops.

In U.S. Pat. Nos. 2,127,879 and 3,122,557 there is described a wide variety of, inter al., 4-hydroxy-coumarin derivatives, similar to a greater or lesser degree to that of the formula I above, the subject of the present invention. The coumarin derivatives described in U.S. Pat. No. 2,127,879 are stated to be effective against a variety of insect pests. Those described in Pat. No. 3,122,557 are said to be bactericides and fungicides and no mention is made of any insecticidal properties being evidenced.

The presently claimed compound, 3-N-(4-trifluoromethylphenyl)-carbamoyl-4-hydroxy-coumarin, which is not specifically mentioned in either of the aforementioned U.S. Patents and which is novel, like its analogues described in U.S. Patent No. 2,127,879, has been found to be active against a wide variety of insects and may be usefull applied against insect pests of, for example, the families:

Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelisae, Coccinellidae, Bruchidae, Scarabaeidae, Dermestidae, Tenebrionidae, Curcullonidae, Tineidae, Noctuidae, Lymantriidae, Pyralidae, Galleridae, Culicidae, Tipulidae, Stomoxydae, Muscidae, Calliphoridae, Trypetidae, and Pulicidae.

Thus, as will appear from the examples hereinafter set forth, it is most effective in combating or controlling insects, or damage caused by insects, of the species *Leptinotarsa decemlineata* (Colorado potato beetle), *Lucilia sericata* (blow fly), *Musca domestica* (house fly), *Chilo suppressalis* (paddy stem borer) and *Aedes aegypti* (yellow feaver mosquito). The compound according to this invention is therefore well suited for application in a variety of fields where insect control is desired, amongst others, the protection of agricultural or horticultural, e.g. vegetable and rice, crops and the treatment of productive live-stock, e.g. cattle.

In accordance with the present invention it has now surprisingly been found that the compound of the formula I, 3-N-(4-trifluoromethylphenyl)-carbamoyl-4-hydroxy-coumarin, whilst possessing a short-term activity against the insect species *Heliothis virescens* (tobacco budworm) which is equal to, or in many instances superior to, that of its previously described analogues has, wholly unexpectedly, a far superior activity against this pest over prolonged periods of time.

For reasons which are presently only poorly understood populations of the insect species *Heliothis virescens*, once a pest of relatively minor importance, have increased massively in the past decade. Today this insect is wide-spread throughout the United States and Central and South America where it causes untold damage to cotton crops. Of all the pests which attack cotton plants it has proved to be one of the most difficult to combat and means for its control has been and continues to be a major concern for the cotton farming industry.

For an analysis of the current situation with respect to this pest, reference may be made to pages 50 to 53 of "The Proceedings of the 1976 Beltwide Cotton Production-Mechanization Conference" published by the National Cotton Council of America, Box 12285, Memphis, Tenn. 38112, from which the following indicative extract is taken.

"The American cotton industry has faced and survived many adversaries throughout its long and successful existence. Today it faces still another. This new adversary, the tobacco budworm, has already tasted victory over the cotton fields of Mexico, periodically caused widespread destruction to cotton production in the Rio Grande Valley of Texas, and in the past two years, left a crippling mark on some of the most productive cotton farms of the Red River Valley of Louisiana. Gentlemen, I am referring to what has come to be regarded as one of the most destructive pests to invade the cotton fields of this country, the Heliothis complex.

The tobacco budworm, *Heliothis virescens (F.)*, and the bollworm, *H. zea* (Boddie), have rapidly replaced the boll weevil, *Anthonomus grandis* (Boheman), as the most dreaded pests in cotton production. Of the two, the tobacco budworm is the most feared and talked about among producers. It is the pest for which most specialists, either Extension or Research Entomologists, are least likely to have a firm answer when asked for control recommendations. Facts are that today we do not have an entirely satisfactory answer to such a question."

Comparatively few agents have been found which are of practical effect against this species. Moreover in areas where chemical pest control have been practiced over a long period of time the situation has been greatly worsened by the appearance of resistant strains, recalcitrant to presently available insecticides. The problem is especially acute in some areas, for example, Texas, where strains of the species Heliothis virescens have developed which are more-or-less wholly resistant to the commonly available organo-phosphate insecticides and the development of alternative insecticides effective against the species Heliothis virescens as well as their testing and clearance has now become a major priority of both the responsible government departments and the chemical industry.

The advantages accruing from the use of insecticides which are effective over a longer period of time are both obvious and well known. Primarily the use of such insecticides results in a reduction in the frequency of treatment (e.g. the adoption of longer spraying intervals) necessary to provide adequate crop protection, with a concommitant saving to the grower and a reduction in the environmental load. With the developing concern in environmental protection, this latter advantage has achieved paramount importance.

The finding that the compound according to the present invention, in addition to its broad effectiveness against insect pests and its broad applicability in e.g. crop and livestock protection, has an excellent long term effect against, particularly, the insect species *Heliothis virescens* is thus seen to be both surprising and important.

The compound of the formula I may be obtained by methods which are known per se, for example by reacting a. a 3-alkoxycarbonyl-4-hydroxy-coumarin of the formula II

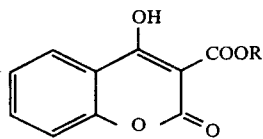

wherein R represents a $C_1$–$C_4$-alkyl group with 4-trifluoromethylaniline; or b. 4-hydroxy-coumarin of the formula III

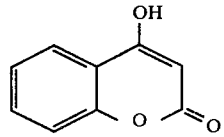

with 4-trifluoromethylphenyl-isocyanat; or by reacting c. 4-hydroxy-coumarin of the formula III above with the azide of the formula IV

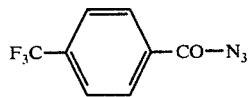

Preferably the processes (a) and (c) are carried out at a reaction temperature between 100° and 200° C and process (b) at a reaction temperature between 0° and 200° C. The reactions can be carried out at normal or elevated pressure, optionally in a solvent or diluent which is inert to the reactants and, if appropriate, in the presence of a base.

Solvents and diluents which are suitable for these reactions are for example: ethers and ethereal compounds, such as dipropyl ether, dioxan, dimethoxyethane and tetrahydrofurane; amides, such as N,N-dialkylated carboxamides; aliphatic, aromatic and halogenated hydrocarbons, in particular benzene, toluene, xylenes, and chlorobenzene; nitriles, such as acetonitrile; dimethyl sulphoxide; and ketones, such as acetone and methyl ethyl ketone.

Suitable bases are tertiary amines, such as triethylamine, dimethyl aniline, pyridine, picolines and lutidines, hydroxides, oxides, carbonates and bicarbonates of alkali metals and alkaline earth metals, for example potassium tert. butylate and sodium methylate.

The insecticidal action of the subject compound can be substantially broadened and adapted to prevailing circumstances by the addition of e.g. other insecticides and/or acaricides. Examples of suitable additives are: organo phosphorus compounds, nitrophenols and derivatives thereof, formamidines, ureas, pyethroids, carbamates, and chlorinated hydrocarbons.

The compound of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, tackifiers, thickeners, binders and/or fertilisers.

For application, the compound of the formula I may be processed to dusts, emulsion concentrates, granules, dispersions, sprays, to solutions or suspensions, in the conventional formulation which is commonly employed in application technology.

The compositions according to the invention are obtained in known manner by intimately mixing and/or grinding the compound of the formula I with the suitable carriers, with or without the addition of dispersants or solvents which are inert to it.

Further the subject compound may, if desired, be processed to one of its salts, e.g. its triethylamine salt, for the purposes of increasing its solubility and compatability in a wider range of formulation types. Such salts may readily be prepared by any of the techniques commonly known and employed in the art.

The subject compound or a salt thereof may for example take, and be used in, the following forms:

Dusts, tracking agents and granules (coated granules, impregnated granules and homogeneous granules);

Liquid forms:

a. active substance concentrates which are dispersible in water, wettable powders, pastes and emulsions; and b. solutions.

The content of active substance in the above described compositions lies generally between 0.1% and 95%, though higher concentrations may also be used if the composition are applied from an aircraft or other appropriate application devices.

The compound (active substance) of the formula I can, for example, be formulated as follows:

Dusts

The following constituents are used to obtain
a. a 5% and b) a 2% dust:

a.  5 parts of active substance, 95 parts of talcum;
b.  2 parts of active substance, 1 part of highly disperse silicic acid, 97 parts of talcum.

The active substance is mixed with the carriers and ground.

Granules

The following constituents are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

Wettable powder:

The following constituents are used for the preparation of a) a 40%, b) and c) a 25%, and d) a 10% wettable powder:

a. 40 parts of active substance, 5 parts of sodium lignin sulphonate, 1 part of sodium dibutyl-naphthalene-sulphonate, 54 parts of silicic acid;

b. 25 parts of active substance, 4.5 parts of calcium lignin sulphonate, 1.9 parts of Champagne chalk/hydroxyethyl cellulose mixture (1:1), 1.5 parts of sodium dibutyl-naphthalene-sulphonate, 19.5 parts of silicic acid, 19.5 parts of Champagne chalk, 28.1 parts of kaolin;

c. 25 parts of active substance, 2.5 parts of isooctyl-phenoxy-polyoxyethylene-ethanol, 1.7 parts of Champagne chalk/hydroxyethyl cellulose mixture (1:1), 8.3 parts of sodium aluminium silicate, 16.5 parts of kieselgur, 46 parts of kaolin;

d. 10 parts of active substance, 3 parts of a mixture of the sodium salts of saturated fatty alcohol sulphates, 5 parts of naphthalenesulphonic acid/formaldehyde condensate, 82 parts of kaolin.

The active substance is intimately mixed, in suitable mixers, with the additives, the mixture being then ground in appropriate mills and rollers to yield wettable powders, which can be diluted with water to give suspensions of the desired concentration.

Emulsifiable concentrate:

The following constituents are used to produce a 10% emulsifiable concentrate:

10 parts of active substance,
3.4 parts of epoxidised vegetable oil,
3.4 parts of a combination emulsifier consisting of fatty alcohol polyglycol ether and alkyl aryl sulphonate calcium salt,
40 parts of dimethylformamide,
43.2 parts of xylene.

By diluting such a concentrate with water it is possible to manufacture emulsions of the desired concentration.

Spray:

The following constituents are used to prepare a) a 5% and b) a 95% spray:

a. 5 parts of active substance, 1 part of epichlorohydrin, 94 parts of benzene (boiling limits 160° C - 190° C;

b. 95 parts of active substance, 5 parts of epichlorohydrin.

The following Examples illustrate the invention in more detail, and are in no way intended to limit the scope of the invention.

EXAMPLE 1

Preparation of 3-N-(4-trifluoromethylphenyl)-carbamoyl-4-hydroxy-coumarin

With stirring, 10.1 g of triethylamine and then 18.6 g of 4-trifluoromethylphenylisocyanate were added dropwise at room temperature to a solution of 16.2 g of 4-hydroxycoumarin in 150 ml of dimethyl sulphoxide. The reaction mixture was stirred for a further 4 hours at room temperature and then poured into a solution of 15 ml of concentrated hydrochloric acid in 300 ml of water. The precipitate which had formed was collected by suction filtration. Recrystallisation from dioxane gave the product of the formula I $$\text{(I)}$$

with a melting point of 258°–260° C.

EXAMPLE 2

Long-term insecticidal activity: Heliothis virescens

Cotton plants were sprayed until dripping with a 0.05% aqueous emulsion of the compound under test, the emulsion having been prepared from a 10% emulsifiable concentrate. After the coating on the cotton plants had dried, each plant was infested with larvae of the species Heliothis virescens at the L3 to L4 instar. Two cotton plants were employed per test substance and the %age mortality achieved was estimated at intervals of 4, 24 and 48 hours after infestation.

In the event that 100% mortality was achieved after 48 hours, the plants were re-infested two days after the original treatment of the plant with the test compound and the %age mortality estimated again at intervals of 4, 24 and 48 hours. If 100% mortality was once more achieved after 48 hours the plants were re-infested for a second time, 8 days after the original treatment of the plant and the %age mortality was again estimated at the same time-intervals as previously.

For the duration of the test the plants were kept at a temperature of 24° C and at 60% relative humidity.

The following results were achieved in a comparative test-run employing the compound according to the present invention and two analogues according to U.S. Pat. No. 2,127,879:

| COMPOUND | Time elapsed after infestation of plant (hrs.) | % MORTALITY | | |
| --- | --- | --- | --- | --- |
| | | Immediate infestation | Infestation 2 days after treatment of plant | Infestation 8 days after treatment of plant |
| The compound according to the present invention. | 4<br>24<br>48 | 0<br>90<br>100 | 0<br>90<br>100 | 0<br>80<br>100 |

| COMPOUND | Time elapsed after infestation of plant (hrs.) | % MORTALITY | | |
|---|---|---|---|---|
| | | Immediate infestation | Infestation 2 days after treatment of plant | Infestation 8 days after treatment of plant |
| [structure: 4-hydroxycoumarin with CO—NH—phenyl]<br>A compound according to U.S. Pat. No. 2'127'879 | 4<br>24<br>48 | 50<br>70<br>70 | —<br>—<br>— | —<br>—<br>— |
| [structure: 4-hydroxycoumarin with CO—NH—(4-chlorophenyl)]<br>A compound according to U.S. Pat. No. 2'127'879 | 4<br>24<br>48 | 0<br>70<br>100 | 0<br>20<br>50 | —<br>—<br>— |

From these test-results it is evident that the compound according to the present invention exhibits a superior activity compared with the two compounds according to U.S. Pat. No. 2,127,879 against larvae of the species *Heliothis virescens* over a prolonged period of time i.e. it has a longer effective life.

EXAMPLE 3

Long-term insecticidal activity: *Leptinotarsa decemlineata*

The procedure of example 2 was repeated exactly using the compound according to the present invention as test-substance, but with larvae of the species *Leptinotarsa decemlineata* (L3 instar) as the test insect and employing potato plants in place of cotton plants. The following results were achieved:

| Time elapsed after infestation of plant (hrs.) | % MORTALITY | | |
|---|---|---|---|
| | Immediate infestation | Infestation 2 days after treatment of plant | Infestation 8 days after treatment of plant |
| 4 | 0 | 0 | 0 |
| 24 | 90 | 50 | 40 |
| 48 | 100 | 100 | 100 |

EXAMPLE 4

Inhibition of damage to plants: *Leptinotarsa decemlineata*

Two potato plants each 15 cm in height were sprayed with 25 ml of an acetone/water mixture (1:1) containing 0.05% of the compound according to the present invention.

After the spray coating had dried, each of the potato plants was infested with 10 larvae of the species *Leptinotarsa decemlineata* at the L3 instar. A plastic cylinder was then slipped over each plant to prevent the larvae from migrating. A copper gauze top was used to seal the cylinder. The damage caused by eating was determined 2 days later.

In this test using the compound of the formula I only trace damage had been caused to the plants by the larvae.

EXAMPLE 5

Inhibition of damage to plants: *Spodoptera littoralis*

The procedure of example 4 was repeated exactly but using larvae of the species *Spodoptera littoralis* (L3 instar) as test insect and 15 cm high cotton plants in place of potato plants.

After treatment with the compound according to the present invention only trace damage was found to have been caused to the test plants after 2 days.

EXAMPLE 6

Insecticidal activity: *Lucilia sericata*

2 ml of an aqueous solution containing 0.1% of the compound of the formula I was added to 2 ml of a culture medium. Approx. 30 freshly hatched-out larvae of *Lucilia sericata* were then added to the culture medium and the insecticidal action was determined after 96 hours by evaluating the mortality rate.

In this test the compound according to the present invention exhibited a positive action against larvae of the species *Lucilia sericata*.

EXAMPLE 7

Insecticidal activity: *Musca domestica*

50 g of freshly prepared CSMA nutrient substrate for maggots were charged into each of three beakers. To each beaker were then added an acetonic solution containing 1% by weight of the compound according to the present invention, the first beaker receiving 5.0, the second 2.5 and the third 0.5 ml of the solution. The nutrient substrate and the acetonic solution were then thoroughly mixed and the beakers left for 20 hours so that the acetone was fully evaporated off.

Thereafter 25 one day-old maggots of the species *Musca domestica* were placed into each of the three beakers. After the maggots had pupated, the pupae were separated from the substrate by flushing them out with water and then deposited in containers closed with a perforated top.

Each batch of flushed out pupae was counted to determine the toxic effect of the active substance on the maggot development and the number of flies which had hatched out of the pupae was then counted after 10 days.

Using the compound according to the present invention in the above test it was found that no living adult flies pupated when the minimum quantity (0.5 ml) of acetonic solution were employed.

EXAMPLE 8

Insecticidal action: *Aedes aegypti*

150 ml of water were introduced into each of six beakers. Quantities of a 0.1% acetonic solution of the compound of the formula I were then pipetted onto the surface of the water in each of the beakers to give a test substance concentration in the first two beakers of 10 p.p.m., in the second two of 5 p.p.m. and in the third two of 1 p.p.m.

After time had been allowed for the acetone to evaporate 30 to 40 larvae of the species *Aedes aegypti* were introduced into each of the six beakers and finally ground food-stuff was added and the beakers covered with a copper-gauze closure. A control-run with two beakers containing no test-substance was conducted simultaneously.

After the controls had shed and emerged fully to the adult stage, the test subjects were examined and the percentage of normal adults was determined.

Using the compound according to the present invention in the above test it was found that no living adults emerged when the minimum concentration of test-substance (1 p.p.m.) was employed.

EXAMPLE 9

Insecticidal action: *Chilo suppressalis*

Rice seedlings of the variety Caloro were reared in plastic pots (6 seedlings per pot) so that their roots became matted to a disc. The roots were then immersed in a 0.08%, 0.02% or 0.01% solution of the compound according to the present invention and allowed to drip off. Then each pot was populated with 5 *Chilo suppressalis* larvae in the L$_2$-stage and the treated plants were subsequently replaced in the pots on top of the larvae.

Evaluation of mortality was made after 5 days and the test was carried out at 24° C and 70% relative humidity.

In the above test the compound according to the present invention gave 100% mortality at the minimum concentration of 0.01%.

I claim:

1. The compound 3-N-(4-trifluoromethylphenyl)-carbamoyl-4-hydroxy-coumarin of the formula I

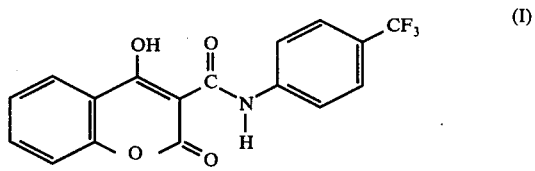

2. An insecticidal composition comprising an insecticidally effective amount of the compound 3-N-(4-trifluoromethylphenyl)-carbamoyl-4-hydroxy-coumarin as claimed in claim 1 together with an appropriate diluent or carrier therefor.

3. A method of controlling insect pests at a locus which method comprises applying to said locus an insecticidally effective amount of the compound 3-N-(4-trifluoromethylphenyl)-carbamoyl-4-hydroxy-coumarin as claimed in claim 1.

4. A method according to claim 3 wherein the locus comprises an agricultural or horticultural crop.

5. A method according to claim 4 wherein the locus comprises a cotton crop.

6. A method of controlling insect pests of the species Leptinotarsa *decemlineata* at a locus which method comprises applying to said locus an insecticidally effective amount of the compound 3-N-(4-trifluoromethylphenyl)-carbamoyl-4-hydroxy-coumarin as claimed in claim 1.

7. A method according to claim 6 wherein the locus comprises an agricultural or horticultural crop.

8. A method according to claim 7 wherein the locus comprises a cotton crop.

* * * * *